United States Patent
Asogawa et al.

(10) Patent No.: US 8,202,722 B2
(45) Date of Patent: Jun. 19, 2012

(54) TEMPERATURE CONTROL METHOD AND SYSTEM

(75) Inventors: Minoru Asogawa, Tokyo (JP); Hisashi Hagiwara, Kanagawa (JP); Tohru Hiramatsu, Nagano (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 12/679,358

(22) PCT Filed: Sep. 16, 2008

(86) PCT No.: PCT/JP2008/067049
§ 371 (c)(1),
(2), (4) Date: Mar. 22, 2010

(87) PCT Pub. No.: WO2009/038203
PCT Pub. Date: Mar. 26, 2009

(65) Prior Publication Data
US 2010/0221814 A1    Sep. 2, 2010

(30) Foreign Application Priority Data
Sep. 21, 2007   (JP) .................................. 2007-245905

(51) Int. Cl.
*C12M 1/38*  (2006.01)
*F28F 13/00* (2006.01)
*F28F 7/00*  (2006.01)

(52) U.S. Cl. ............. 435/303.1; 165/135; 165/185; 435/286.1; 435/286.5

(58) Field of Classification Search ........... 435/303.1, 435/286.1, 286.5; 165/135, 185
See application file for complete search history.

(56) References Cited

U.S. PATENT DOCUMENTS

| | | | |
|---|---|---|---|
| 4,627,554 A * | 12/1986 | Leibinsohn | 222/103 |
| 7,186,084 B2 * | 3/2007 | Bunker et al. | 416/96 R |
| 2004/0047769 A1 | 3/2004 | Tanaami | |
| 2005/0153430 A1 | 7/2005 | Ohtaka | |
| 2006/0246573 A1 | 11/2006 | Kurane et al. | |
| 2009/0136963 A1 * | 5/2009 | Breidenthal et al. | 435/6 |

FOREIGN PATENT DOCUMENTS

JP    4-215978    8/1992
(Continued)

OTHER PUBLICATIONS

Machine translation of Numata et al. (JP 2006-262788).*
(Continued)

*Primary Examiner* — Nathan Bowers
*Assistant Examiner* — Gautam Prakash
(74) *Attorney, Agent, or Firm* — Young & Thompson

(57) ABSTRACT

For heating or cooling a sample contained in a vessel portion through a heat transfer member held in contact with the vessel portion, there is used the vessel portion, which has a part formed of an elastic member, expands and contracts for injection and discharge of the sample, is closed other than a connecting port with a channel connected to the vessel, and expands and contracts for injection and discharge of the sample. The vessel portion expands correspondingly to the injection when the sample is injected through an inflow path serving as the channel into the vessel portion contracting in a non-contacting state with the heat transfer member. A predetermined amount of sample is injected into the vessel portion so as to expand the vessel portion, and the vessel portion comes into contact with the heat transfer member. The vessel portion is heated or cooled through the heat transfer member.

11 Claims, 17 Drawing Sheets

FOREIGN PATENT DOCUMENTS

| | | |
|---|---|---|
| JP | 2002-365299 | 12/2002 |
| JP | 2004-309405 | 11/2004 |
| JP | 2005-040784 | 2/2005 |
| JP | 2005-117988 | 5/2005 |
| JP | 2005-176836 | 7/2005 |
| JP | 2005-214782 | 8/2005 |
| JP | 2005-264507 | 9/2005 |
| JP | 2006-262788 | 10/2006 |

OTHER PUBLICATIONS

International Search Report, PCT/JP2008/067049, Dec. 2, 2008.

* cited by examiner

TEMPERATURE CONTROL METHOD AND SYSTEM

TECHNICAL FIELD

This invention relates to a technology, in which a vessel is provided to a chip which is called a microchip or a micro array, and the vessel is packed with a micro component to be heated or cooled so as to cause a reaction of the micro component, thereby obtaining a desired product. Such technology is used for amplifying a polymerase chain reaction (PCR) of a DNA, for example.

BACKGROUND ART

In recent years, there has been proposed a technology, in which an extremely small plate-shape portion (hereinafter, referred to as a microchip) called a microchip or a micro array is provided with a micro sample vessel, and solution delivery is performed in the microchip so as to perform mixing and reaction. The sample vessel of the microchip of this type has a diameter of 1 to 2 mm and a capacity of 2 to several μL, and is intended for an extremely small amount of sample.

Meanwhile, there has been already proposed a method of obtaining a desired product, in which the sample packed in minute volume vessel is subjected to a heating and cooling temperature cycle for extraction and analysis of a gene or a nucleic acid.

In Japanese Unexamined Patent Application Publication (JP-A) No. 2005-117988 (hereinafter, referred to as Patent Document 1), there is described that "a device for amplifying a DNA including a treating block constructed of a substrate part keeping contact with a heating and cooling side of a thermo module, and formed by using a ceramic material and/or a graphite material having a thickness set to about ≦3 mm, and one or more cell part arranged on an upper face of the substrate part and composed of a material different from the ceramic material and the graphite material". The device for amplifying a DNA installs therein the cell part having a cup-shape. There is described that "the cell part is a vessel of about 0.2 to 1.5 mL, and the cell parts are a plurality of recessed portions, which are formed on the upper surface of the plane board superposed on the upper surface of the substrate part".

In Japanese Unexamined Patent Application Publication (JP-A) No. 2005-40784 (hereinafter, referred to as Patent Document 2), there is described that a temperature controlling mechanism in which, for each of the two or more chemical reaction parts in the microchemical chip, through a thermal conductor installing therein a temperature measuring means, a thermoelectric element is applied with a load so as to come into contact with a chemical reaction part in the microchip as a temperature generator. Upon temperature control, the thermoelectric element or the thermal conductor is caused to come into contact with the chemical reaction part. In this case, the both are caused to come into contact with each other by being loaded by a supporting member formed of an elastic body such as a spring. Further, the thermal conductor is exposed into the atmosphere, a part thereof is inserted into the recessed portion of the microchemical chip. Further, when the sample delivered to the reaction part in the microchemical chip is heated, the sample is heated in a state in which portions to be applied with heat such as a sample part, a conveying path, and a solvent part are continuous with and opened to each other.

DISCLOSURE OF THE INVENTION

Problems to be Solved by the Invention

A cell described in Patent Document 1 is generally called a cup or a tube, and is intended for a capacity of about 0.2 to 1.5 mL as described above. When such cell is used for heating or cooling the sample having a volume of 2 to several μL, there arises a problem in that a heat transfer efficiency of an amount of heat generated by the thermo module generating heat in a space between the adjacent cells is low. In Patent Document 1, though a vessel portion, which is set as a groove having a recessed shape, is also described, there arises also a problem in that the heat transfer efficiency of the amount of heat generated by the thermo module in the space between the adjacent cells is low even with the groove-like vessel.

Further, the vessels on the microchip have a extremely small volume, and, for the purpose of a compacted device, the vessels are required to be installed at an extremely small interval, and a reaction time is required to be reduced. In particular, the reaction time of PCR amplification depends on the temperature cycle repeated about 30 times, and hence it is required that all amount of heat of the heat-generating surface of the thermo module is efficiently collected into the sample vessel at a pin point.

Further, in a case where the sample vessel to be heated is provided in the microchip, its capability is an extremely small volume of several microlitters. When the sample of extremely small amount is heated, the inside of the sample vessel achieves a high temperature and a high pressure, and hence leakage from the channel for inflow and outflow is easy to occur. Therefore, there is required a means for sealing the sample vessel upon heating.

With a load means using the supporting member formed of the elastic body such as the spring, for controlling the temperature of a plurality of reaction parts provided in the microchemical chip, due to variation of accuracy of the microchemical chip and variation of positional accuracy upon mounting, a pressure-contact-force between the reaction parts and the thermal conductor, is ununiform, and hence there arises a problem in that temperature control is difficult. Further, compactification of the device installing therein the microchemical chip is difficult. For example, with reference to FIG. 1 in Patent Document 2, in this structure, the movable member 109 presses the microchemical chip 101 to the lower side through an elastic body 108, and hence the lower part of the reaction part 102 and the thermal conductor 104 are kept being contacted with each other. Therefore, even for the purpose of adjusting the contacting state in the lower part of the reaction part 102, the entire of the microchemical chip 101 must be adjusted, and hence adjusting is difficult. In particular, in a case where the plurality of reaction parts are arranged on the microchemical chip, all contacting state in the lower part of the plurality of reaction parts must be adjust at one time by adjusting the position and the angle of the entire of the microchemical chip, and hence adjusting is difficult. Further, due to the structure in which the microchemical chip is pressed through the elastic body, compactification of the device is difficult.

Further, in a case where the thermal conductor is exposed to the atmosphere and the part thereof is inserted into the recessed portion of the microchemical chip, a loss of radiating heat to the surrounding area is large, and hence there arises a problem in that the heat transfer efficiency is decreased.

In addition, when the sample delivered to the reaction part in the microchemical chip is heated in a state in which the portions to be applied with heat such as the sample portion, the conveying path, and the solvent portion are continuous with and opened to each other, the sample expands due to heating. As a result, the sample leaks into the conveying path and moves therein, and hence there arises a problem in that it is impossible to efficiently control the temperature of the sample.

This invention has been made in view of the above-mentioned circumstance, and a problem to be solved by this invention is to provide the following: a temperature control method, in which it is possible to efficiently heat and radiate heat when an extremely small amount (that is, about several microlitters) of sample is heated or cooled, and it is possible to prevent leakage even at a high temperature and under high pressure when an extremely small amount of sample is heated; a temperature control system including such sample vessel; and a microchip including such sample vessel.

Means to Solve the Problems

In order to solve the above-mentioned problem, this invention provides, as a temperature control method of heating or cooling a sample contained in the vessel portion through a heat transfer member held in contact with the vessel portion, one having the following characteristics. According to the temperature control method, at least one part of the vessel portion (elastic vessel 70e) is formed of an elastic member. The vessel portion is closed other than a connecting port with a channel connected to the vessel portion. The vessel portion expands and contracts correspondingly to injection and discharge of the sample. Further, the temperature control method includes each of the following stages. That is, the temperature control method includes a stage, at which, when a sample is injected through an inflow path serving as a channel into the vessel portion (FIG. 3) contracting in a non-contacting state with the heat transfer member, the vessel portion expands correspondingly to injection (FIG. 5), a stage, at which the vessel portion, into which that a predetermined amount of sample is injected into so as to expand, comes into contact with the heat transfer member (FIG. 5), and a stage, at which the vessel portion is heated or cooled through the heat transfer member (FIG. 6). Further, a temperature control system and a microchip for performing temperature control according to the temperature control method are also provided.

Effect of the Invention

According to this invention, the sample vessel formed of an elastic material is caused to expand like a balloon by injection of the sample so that one end of the sample vessel comes into contact with the heat transfer body or the heat generator. With this, it is possible to efficiently heat and cool the sample. In the field of analyzing a gene, a PCR amplification step for amplifying a DNA is conducted. PCR amplification is a step of applying a temperature cycle of a high temperature (as one example, 97° C.) and a low temperature (as one example, 53° C.) to the sample about 30 times. If the elastic vessel portion of this invention is set as the PCR amplification reservoir, it is possible to efficiently heat and cool the sample, and hence it is possible to shorten a period of the temperature cycle and to improve the productivity.

Further, according to this invention, it is possible that a pressure generated from the sample due to heating is restrained by elasticity of the vessel so as to prevent the sample from leaking.

Further, according to this invention, due to improvement of the heating and cooling efficiency, it is possible to compactify the device and save energy.

In addition, according to this invention, the contacting state between the vessel portion and the heat transfer member is kept due to a pressure generated due to expansion when the sample is injected into the vessel portion, and hence it is possible to heat or cool an extremely small subject-vessel. In particular, even a case where the plurality of vessels are arranged in an extreme vicinity of the heat transfer member, the contacting state between the vessel portion and the heat transfer member is adjusted for each of the vessel portions. Thus, in all vessel portions on the identical microchip, the contacting state between the vessel portion and the heat transfer member is satisfactorily kept, and hence it is possible to compactify the microchip.

Further, according to this invention, the sample is packed in the balloon-like vessel and heated or cooled therein, and hence it is possible to heat or cool, even in a zero gravity space such as the space or in water, the sample without scattering the sample. Further, due to the same reason, it is possible to heat or cool, even in high pressure ambience such as the deep-sea, the sample.

Figure 14:
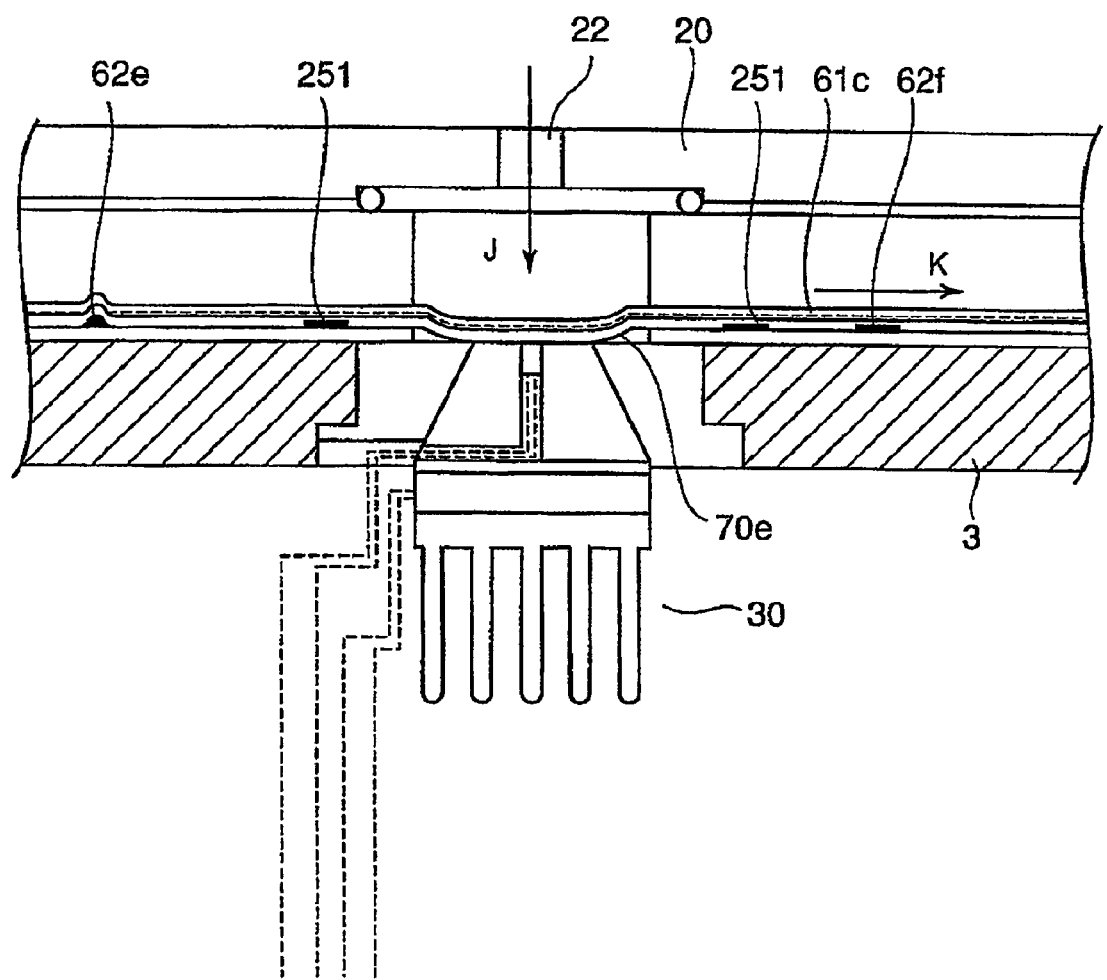

FIG. 14 is a cross-sectional view for illustrating, in the microchip 250, a state in which the shutter channel 62e is closed, the shutter channel 62f and the closed channel 251 are opened, and a pressure is applied to the elastic vessel portion 70e from the direction J so as to discharge the sample to the direction F.

Figure 15:
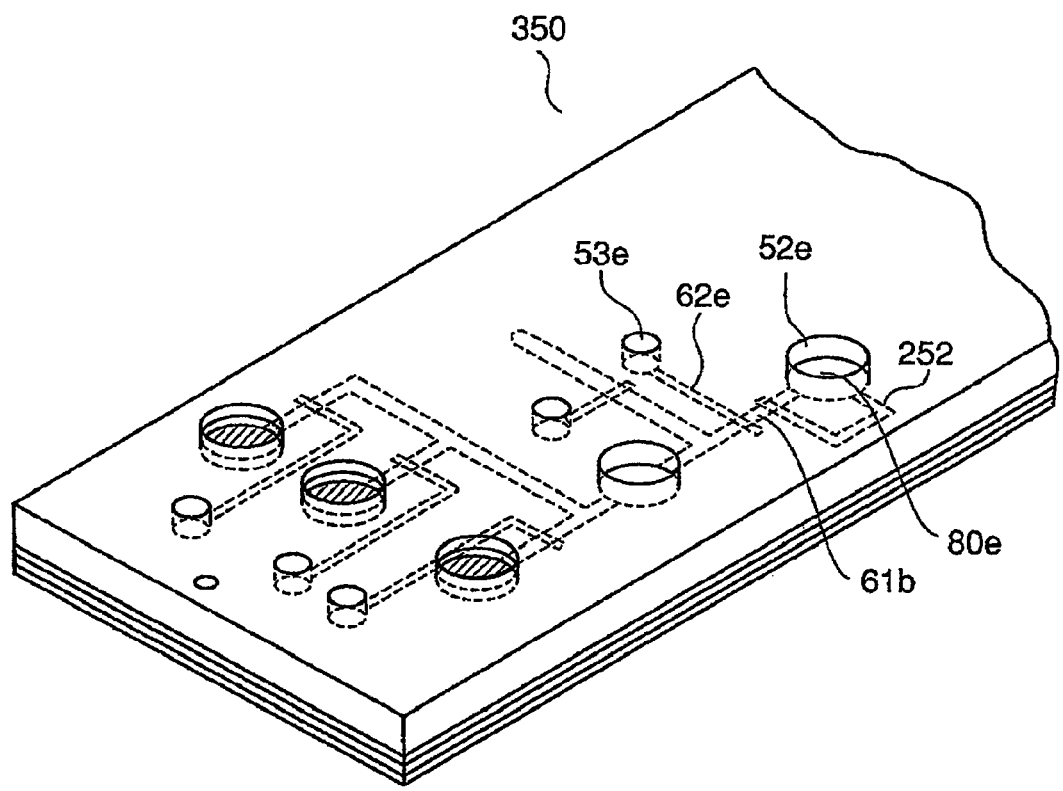

FIG. 15 is a perspective view of a part of a microchip 350 of Embodiment 3.

Figure 16:
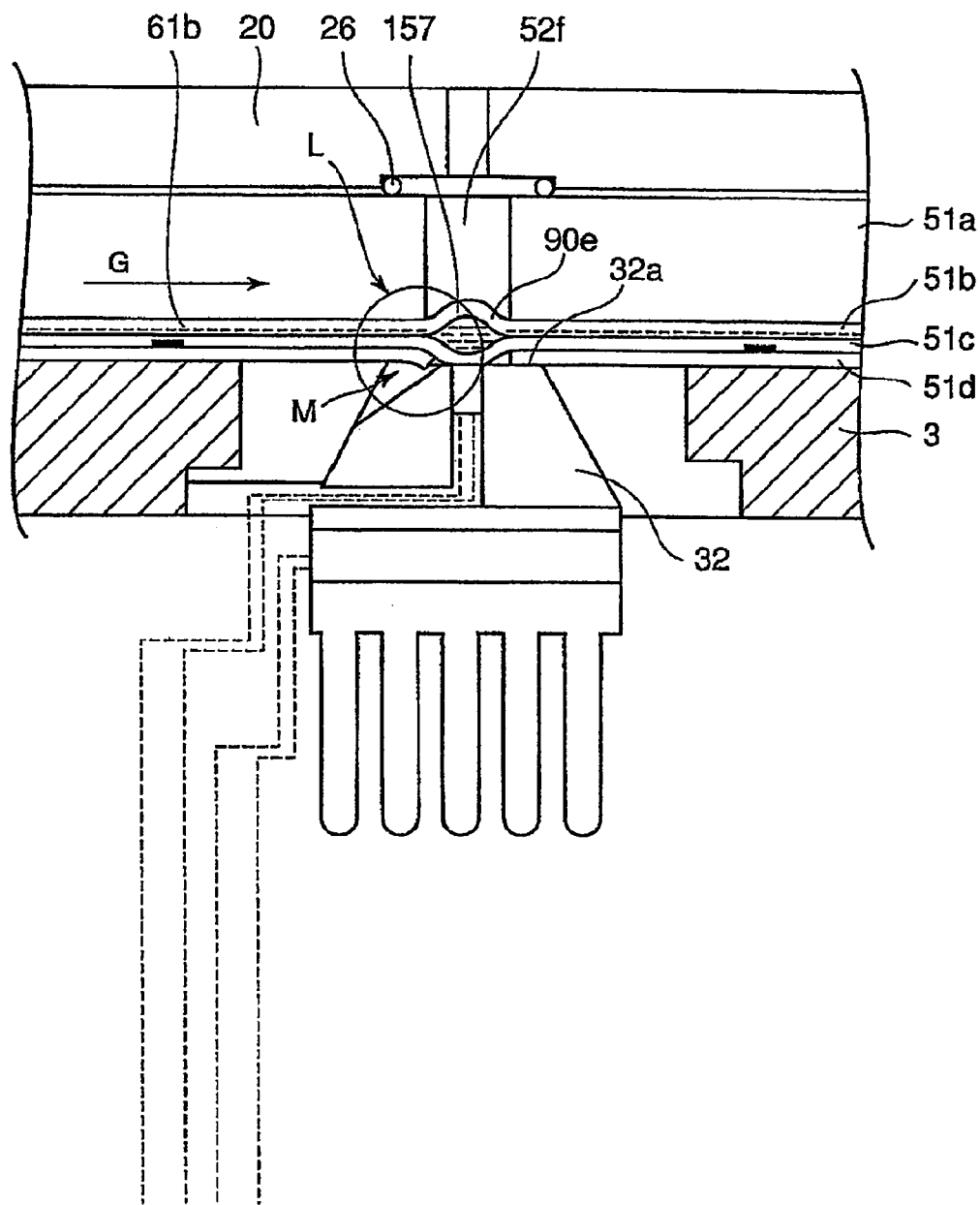

FIG. 16 is a cross-sectional view for illustrating a cutout M formed on a cutout M of the narrow surface 32a of the heat transfer member 32 of Embodiment 4.

Figure 17:
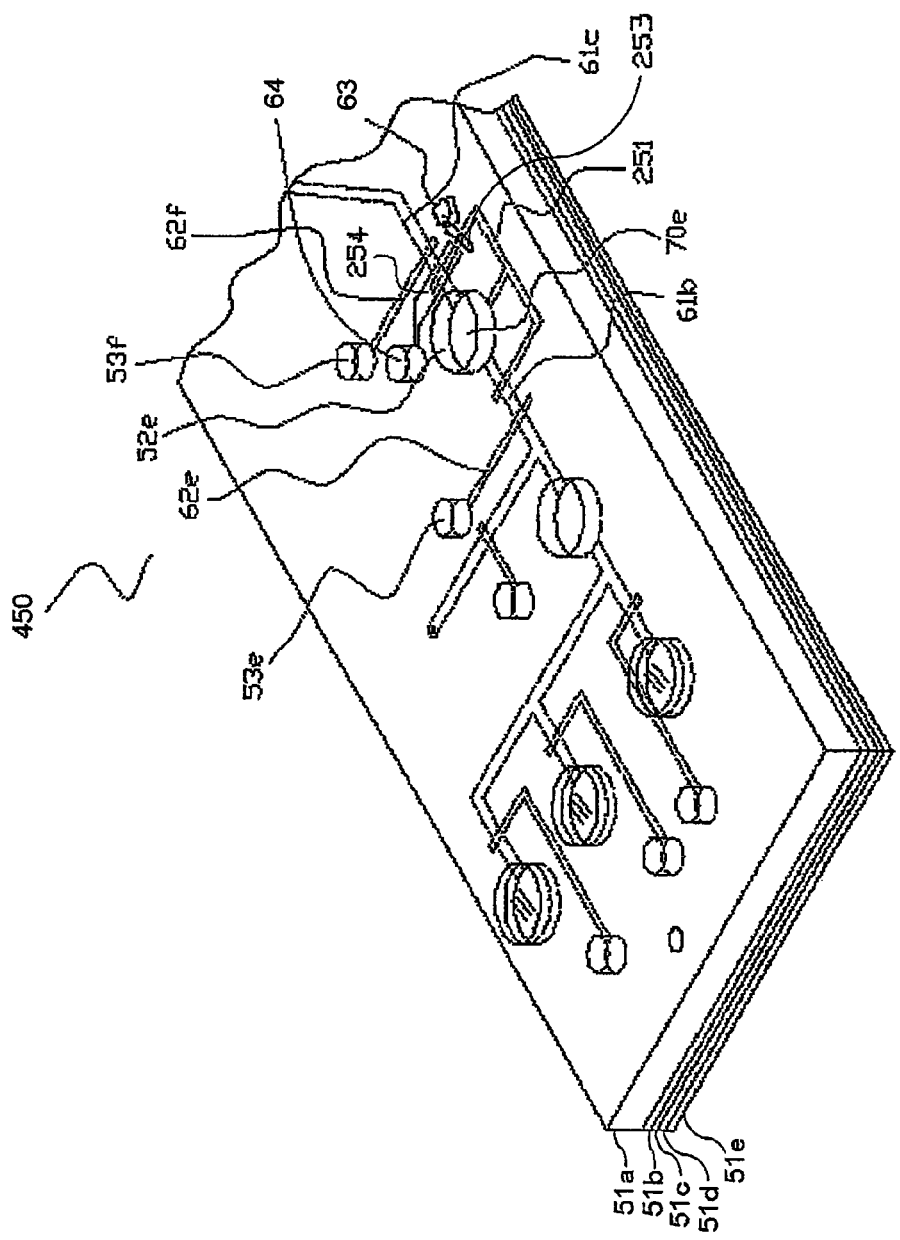

FIG. 17 is a perspective view of a part of a microchip 450 of Embodiment 5.

BEST MODE FOR EMBODYING THE INVENTION

This invention is described in the following with reference to the embodiments.

Embodiment 1

Figure 1:
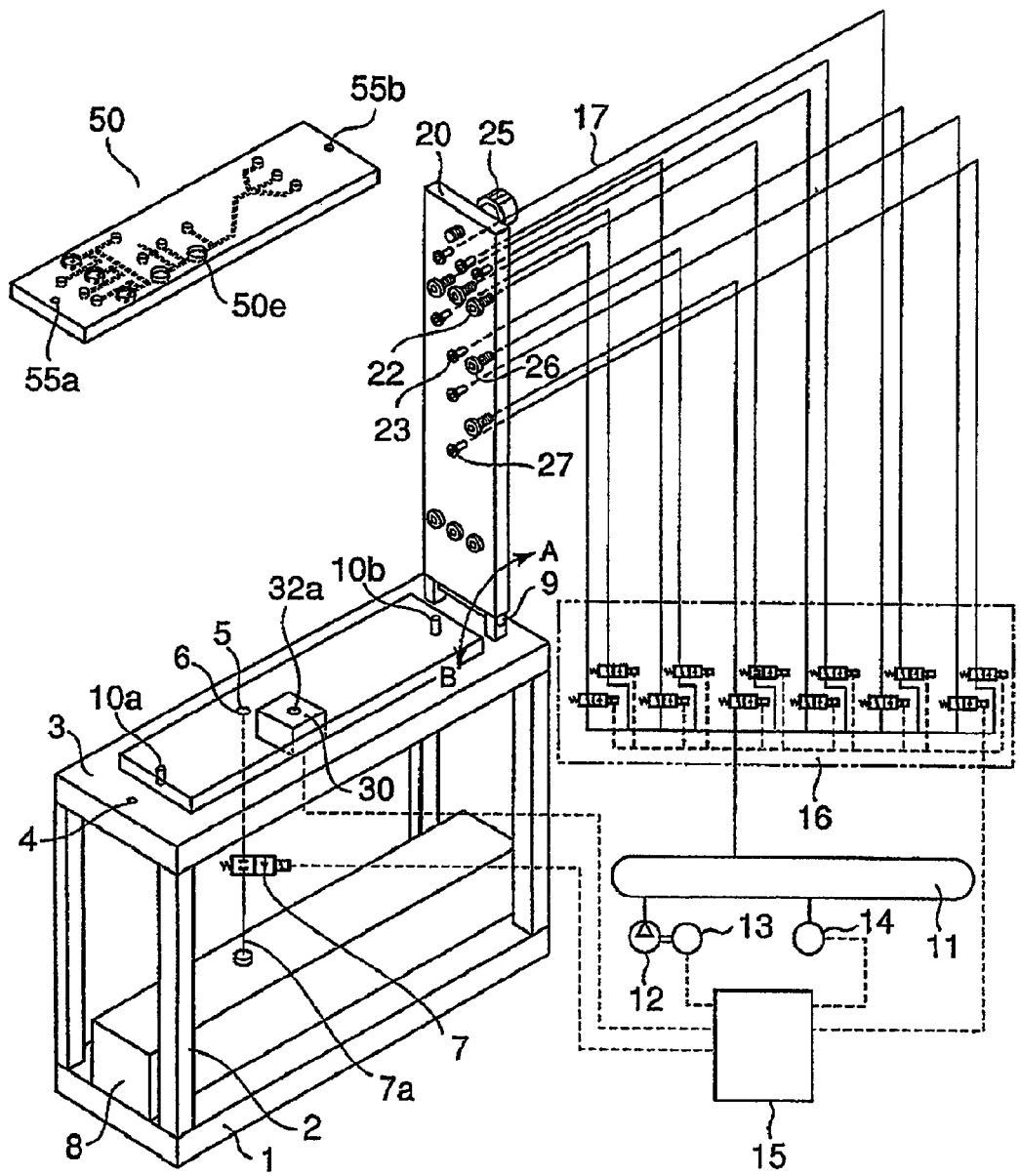
FIG. 1 is a perspective view and a diagram of a logic circuit of an analysis device and a microchip 50 according to Embodiment 1 of this invention.

Embodiment 1 of this invention is described. Embodiment 1 includes an analysis device illustrated in the perspective view of FIG. 1 and a microchip 50 containing a sample to be analyzed by the analysis device. In FIG. 1, pneumatic circuit portions are indicated by logical symbols based on JIS. On a machine casing 1, a table 3 is provided through poles 2. Further, in a table 3, a disposal hole 5 whose periphery is sealed by an O-ring 6 is provided. Further, the disposal hole 5 is connected to a disposal reservoir 8 provided onto the machine casing 1 through a disposal solenoid-controlled valve 7 and a tube 7a. Further, in an upper surface of the table 3, pins 10a and 10b corresponding to pin holes 55a and 55b provided in the microchip 50 to serves as a guide to a predetermined position are provided in a protruding manner. Further, on the table 3, through a hinge 9, there is provided, so as to be rotatable to the directions A and B, a cover 20 having a fastening screw 25, a plurality of pressurizing holes 22 which pass through a cover 20 and is sealed by an O-ring 26 from the peripheries thereof, a plurality of shutter pressurizing holes 23 sealed by an O-ring 27 from the peripheries thereof, and the cover 20 having an O-ring 31. Further, in one end on the table 3, a screw hole 4 is provided at a position corresponding to the fastening screw 25 to constitute a mechanism capable of sandwiching and fixing the microchip 50 to a predetermined position.

In addition, a plurality of pressing holes 22 and a plurality of shutter pressurizing holes 23, which are provided while passing through the cover 20, are connected to secondary sides of a driving unit 16 constituted by a plurality of solenoid-controlled valves through a plurality of tubes 17, respectively. Further, primary sides of the solenoid-controlled valves are connected to a pressure accumulator 11. Further, to the pressure accumulator 11, there are connected a pump 12 driven by a motor 13 and a pressure sensor 14 for detecting inner pressure. Further, on the table 3, there is provided a temperature adjusting unit 30 for controlling a position from the lower surface thereof to a predetermined temperature while the narrow surface 32a being exposed to the outside, the position corresponding to the extraction reservoir 52e to be heated in the microchip 50 when the microchip 50 is mounted.

Meanwhile, to a controller 15 for executing a predetermined program, there are connected, so as to be operationally controlled, solenoid-controlled valves of the driving unit 16 and disposal solenoid-controlled valve 7. Further, to the controller 15, the motor 13 and the pressure sensor 14 are connected, the motor 13 driving the pump 12 so as to control the pressure in the pressure accumulator 11 to a predetermined pressure, and the pressure sensor 14 detecting the pressure in the pressure accumulator 11 to perform feedback. With the above-mentioned structure, due to instructions from the controller 15, the pressure in the pressure accumulator 11 is constantly kept in a predetermined pressure. In addition, in this configuration, the solenoid-controlled valves in the driving unit 16 is driven in accordance with a preset program, to thereby pressurize and apply a pressure medium, which is typified by the air in the pressure accumulator 11, to a pressurizing hole 22 and a shutter pressurizing hole 23. Further, in this structure, the temperature adjusting unit 30 is similarly connected to the controller 15, to thereby perform a temperature control programmed in advance.

Figure 2:
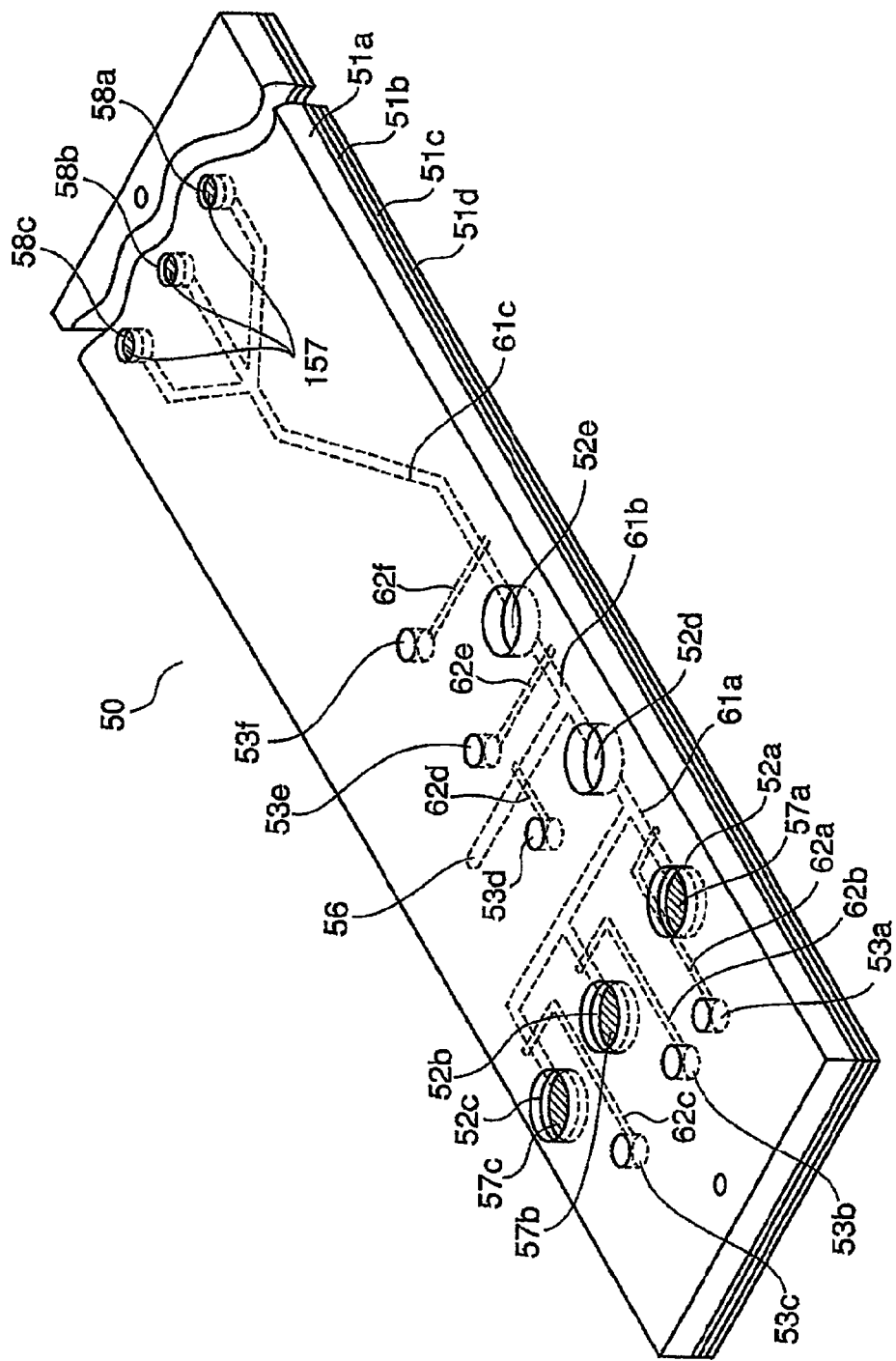
FIG. 2 is a perspective view illustrating a mechanism structure of the microchip 50.

FIG. 2 is a perspective view illustrating details of the microchip 50. The microchip 50 has a multi-layer structure, in which a main plate 51a, a second plate 51b, a third plate 51c, and a fourth plate 51d, each being made of an elastic member, are laminated together.

On the microchip 50, there are provided sample reservoirs 52a, 52b, and 52c which pass through the main plate 51a and the second plate 51b to be formed into recessed shapes, and is packed with the sample in advance, and outlet ports 58a, 58b, and 58c. In addition, there are provided a reaction reservoir 52d and the extraction reservoir 52e, which have structures of passing through the main plate 51a and the fourth plate 51d, and not passing through the second plate 51b and the third plate 51c, but sandwiching the second plate 51b and the third plate 51c therebetween. The detailed structure is described later. Further, on the microchip 50, there are provided shutter ports 53a, 53b, 53c, 53d, 53e, and 53f passing through the main plate 51a, the second plate 51b, and the third plate 51c to be formed into recessed shapes. Further, a chip disposal hole 56 is provided so as to pass through the second plate 51b, the third plate 51c, and the fourth plate 51d to a lower direction. Further, when the microchip 50 is installed on the table 3 illustrated in FIG. 1, and the cover 20 is rotated to a B direction, to thereby sandwich the microchip 50 between the table 3 and the cover 20 by the fastening screw 25 and the screw hole 4, the sample reservoirs 52a, 52b, and 52c, the reaction reservoir 52d, the extraction reservoir 52e, and the shutter ports 53a, 53b, 53c, 53d, 53e, and 53f are installed at positions corresponding to the pressurizing holes 22 and the shutter pressurizing holes 23.

In addition, the sample reservoirs 52a, 52b, and 53c, the reaction reservoir 52d, the extraction reservoir 52e, and outlet ports 58a, 58b, and 58c are continuous through channels 61a, 61b, and 61c formed between the main plate 51a and the second plate 51b. Further, the shutter ports 53a, 53b, 53c, 53d, 53e, and 53f are continuous with the shutter channels 62a, 62b, 62c, 62d, 62e, and 62f formed between the second plate 51b and the third plate 51c. Further, leading ends thereof are provided so as to intersect with the channels 61a, 61b and 61c through the third plate 51c. That is, in this structure, when the pressure medium typified by the air is pressurized and applied to the shutter ports 53a, 53b, 53c, 53d, 53e, and 53f, the shutter channels 62a, 62b, 62c, 62d, 62e, and 62f close the channels 61a, 61b, and 61c at the intersecting portions. Further, in this mechanism, when application of the pressure medium is released, the intersecting portions are opened. In addition, sample reservoirs 52a, 52b, and 52c are packed with samples 57a, 57b, and 57c, respectively.

Further, the channels 61a, 61b, and 61c and the shutter channels 62a, 62b, 62c, 62d, 62e, and 62f are structured so that their linear portions in the plates, of which each of the channels 61a, 61b, and 61c and the shutter channels 62a, 62b, 62c, 62d, 62e, and 62f are formed, are not bonded with each other, and have no volume in a state in which the sample is not delivered.

With the above-mentioned structure, after the microchip 50 is installed and fixed on the device illustrated in FIG. 1, when operation instructions, which are programmed in advance, is sent from the controller 15, the driving unit 16 and the disposal solenoid-controlled valve 7 performs a sequential operation, and the channels 61a, 61b, and 61c required for solution delivery is sequentially opened/closed through the shutter channels 53a, 53b, 53c, 53d, 53e, and 53f, to thereby perform solution delivery operation. As a result, the samples 57a, 57b, and 57c illustrated in FIG. 2 are sequentially delivered to the reaction reservoir 52d and the extraction reservoir 52e, or an unnecessary sample is disposed of from a chip-disposal-hole 56, and the temperature control mechanism of this invention is driven in the extraction reservoir 52e. After that, the sample 157 having a desired minute amount is delivered to the outlet ports 58a, 58b, and 58c and is packed therein. The detailed description of a programmed operation for solution delivery is omitted.

Figure 3:
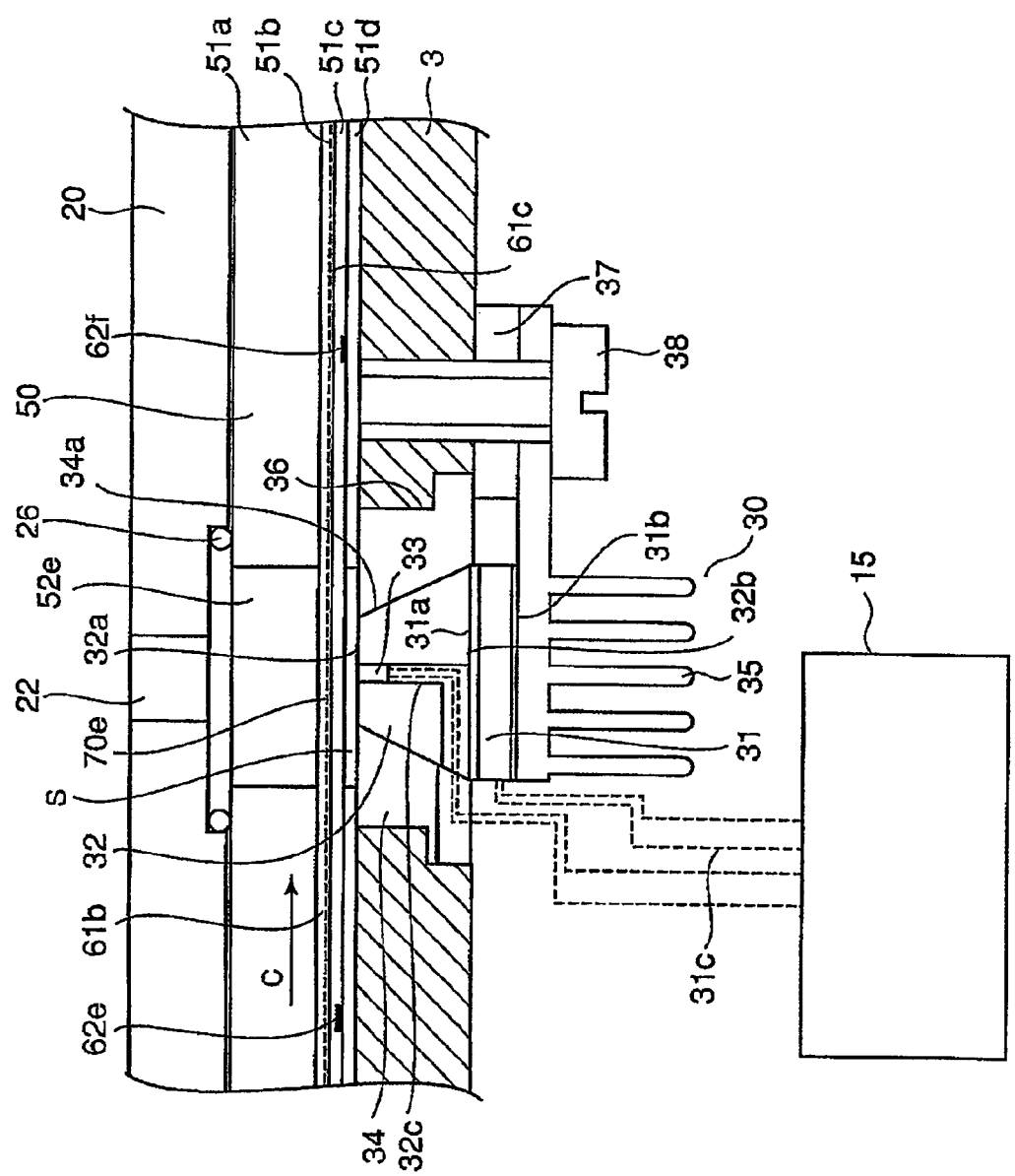
FIG. 3 is a cross-sectional view of an extraction reservoir 52e and an elastic vessel portion 70e provided to the microchip 50, and a temperature control unit of the analysis device.

Details of the extraction reservoir 52e and a temperature control unit 30 are described with reference to a cross-sectional view of FIG. 3. FIG. 3 illustrates a state before the sample is packed in the extraction reservoir 52e. The microchip 50 is sandwiched between the table 3 and the cover 20 through an O-ring 26. The extraction reservoir 52e provided to the microchip 50 is sandwiched while a hole passing through the main plate 51a and the fourth plate 51d of the microchip 50 does not pass through the second plate 51b and the third plate 51c. Further, the elastic vessel portion 70e in the extraction reservoir 52e causes portions of the second plate 51b and the third plate 51c having substantially the same diameter as those of through-holes of the main plate 51a and the fourth plate 51d not to bond thereto. In addition, the channels 61b and 61c are provided between the second plate 51b and the third plate 51c in a state in which linear portions are not bonded, and the channels 61b and 61c are continuous to the elastic vessel portion 70e. That is, with this structure, the sample delivered into the channel 61b to a C direction is guided into the elastic vessel portion 70e.

In addition, the shutter channels 62e and 62f are provided between the third plate 51c and the fourth plate 51d in a state in which linear portions are not bonded, and the shutter channels 62e and 62f are provided to a lower direction of the channels 61b and 61c so as to form an intersecting portion. Further, the fourth plate 51d constituting a lowermost portion of the microchip 50 is provided with a through-hole, and hence a gap portion S is interposed between the third plate 51c constituting a part of the elastic vessel portion 70e and the narrow surface 32a of the heat transfer member 32, whose surface is flush with an upper surface of the table 3. For the sake of description, the channels 61b and 61c and the shutter channels 62e and 62f are illustrated as portions having real bodies. However, actually, their capacity is zero.

In addition, details of the temperature control unit 30 are described. Into a through-hole 36 formed in the table 3, a heat insulating member 34 is inserted. Further, in a truncated-cone-like through-hole 34a formed in the heat insulating member 34, the heat transfer member 32 formed into a truncated cone shape is fitted. That is, the side surface of the heat transfer member 32 is covered with the heat insulating member 34. With this, the side surface of the heat transfer member 32 is prevented from being exposed to the atmosphere, and hence heat conduction efficiency by the heat transfer member 32 can be enhanced. Further, a small hole 32c is provided in the heat insulating member 34, and a temperature sensor 33 is embedded therein so that a tip end thereof is flush with the narrow surface 32a of the heat transfer member 32. On the other hand, a Peltier element 31, which is a well known portion as an electrical current/heat one-way conversion element, is provided so that a heat applying surface 31a is held in contact with a wide surface 32b of the heat transfer member 32, and a heat radiation surface 31b on the other surface is held in contact with a heat radiation plate 35. In addition, the heat radiation plate 35 is fixed to the table 3 through a screw 38 and a pedestal 37.

In addition, power wires 31c of the temperature sensor 33 and the Peltier element 31 are connected to the controller 15. That is, a configuration is obtained in which the Peltier element 31 is feedback-controlled from the temperature sensor 33 as programmed by the controller 15 in advance so as to be heated or cooled, to thereby transfer heat to the heat transfer member 32. Further, with this configuration, the heat transfer member 32 is allowed to collect heat or disperse heat. Details thereof are described later.

Figure 4:
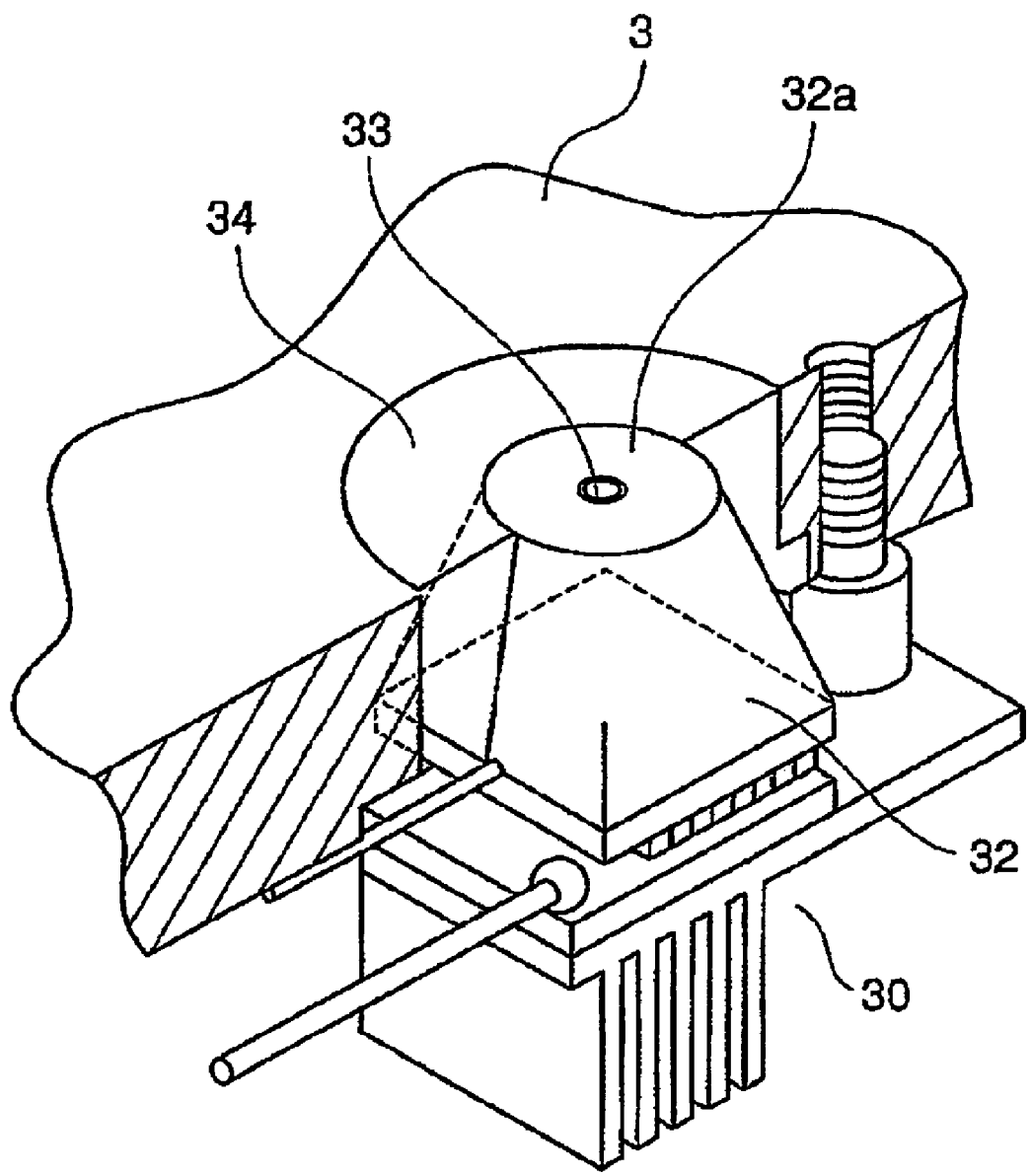
FIG. 4 is a perspective view of a cross-section of the temperature control unit.

In addition, with reference to FIG. 4, installation of the temperature control unit 30 in the table 3 is described in detail. FIG. 4 is a partially cross-sectional perspective view. The narrow surface 32a of the heat insulating member 34 constituting the temperature control unit 30, the tip end of the temperature sensor 33, and an end surface of the heat insulating member 34 are formed so as to be flush with the upper surface of the table 3.

Next, there is described an operation in which the extraction reservoir 52 is packed with the sample, and a predetermined temperature is applied to the extraction reservoir 52 by the temperature control unit 30. As described above, the samples which are finished being reacted after the samples 57a, 57b, and 57c packed in the reaction reservoirs 52a, 52b, and 52c illustrated in FIG. 2 are sequentially delivered to the reaction layer 52d are extruded into the channel 61b by being pressurized and applied with a pressure medium typified by the air from the upper side of the reaction layer 52d. In this time, the shutter channel 62d is closed. Further, the shutter channel 62e is opened, and the shutter channel 62f is closed. As a result, the sample is injected into the extraction reservoir 52e through the exclusively opened channel, that is, the channel shutter channel 62e.

Figure 5:
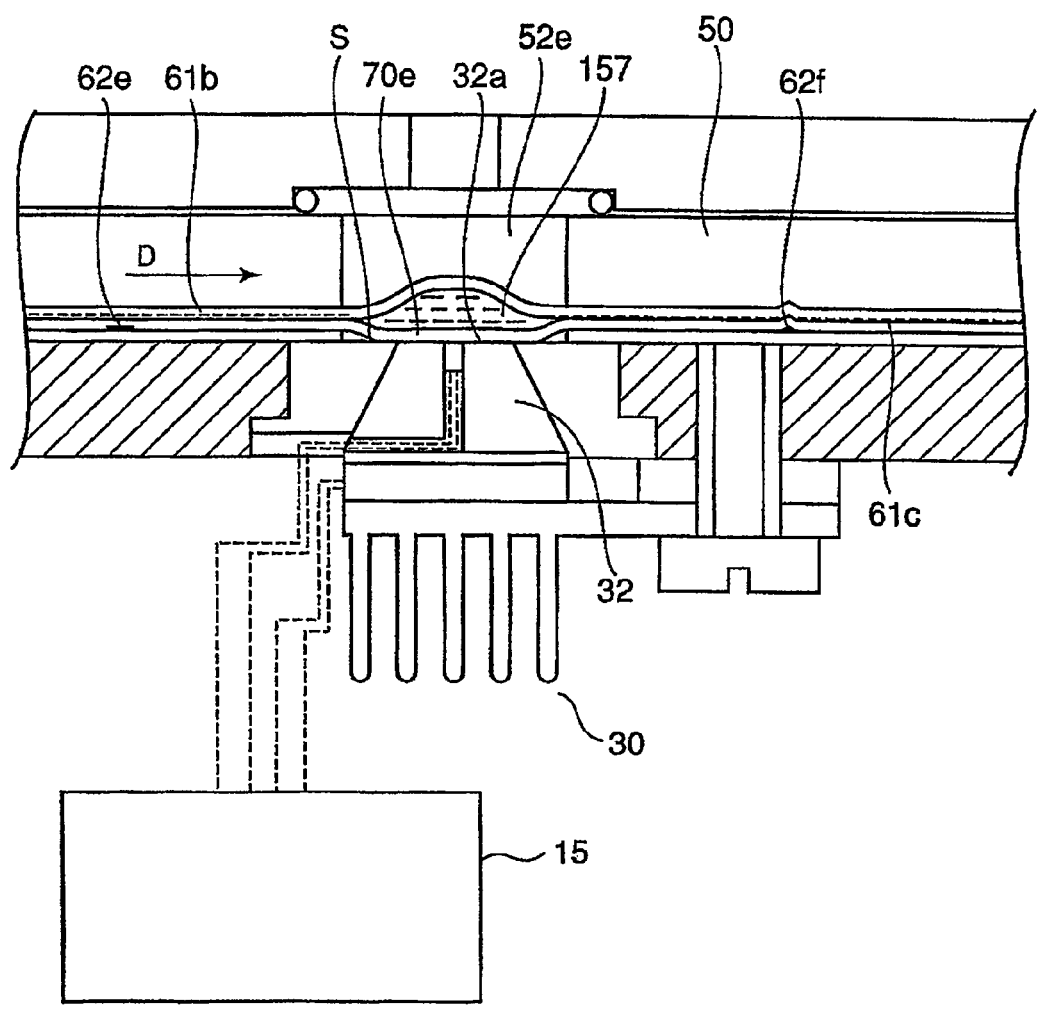
FIG. 5 is a cross-sectional view for illustrating, in Embodiment 1, a step of opening a shutter channel 62e, closing a shutter channel 62f, and injecting a sample into the elastic vessel portion 70e.

More detailed operation is described with reference to FIG. 5. FIG. 5 is a cross-sectional view illustrating details of the extraction reservoir 52e and the temperature control unit 30. Because the shutter channel 62e is opened as described above, the sample 157 extruded from the reaction vessel 52d to the D direction is guided through the channel 61b to the elastic vessel portion 70e constituting the extraction reservoir 52e. Further, the pressure medium is pressurized and applied to the shutter channel 62f so as to deflect the third plate 51c, and hence the outflow channels 61c from the elastic vessel portion 70e is closed. As a result, the sample 157 expands the elastic vessel portion 70e like a balloon, to be packed therein. In addition, a part of the elastic vessel portion 70e expands to the lower side and protrudes into an interior of the space portion S so as to pressure-contact the narrow surface 32a of the heat transfer member 32 constituting the temperature control unit 30.

Figure 6:
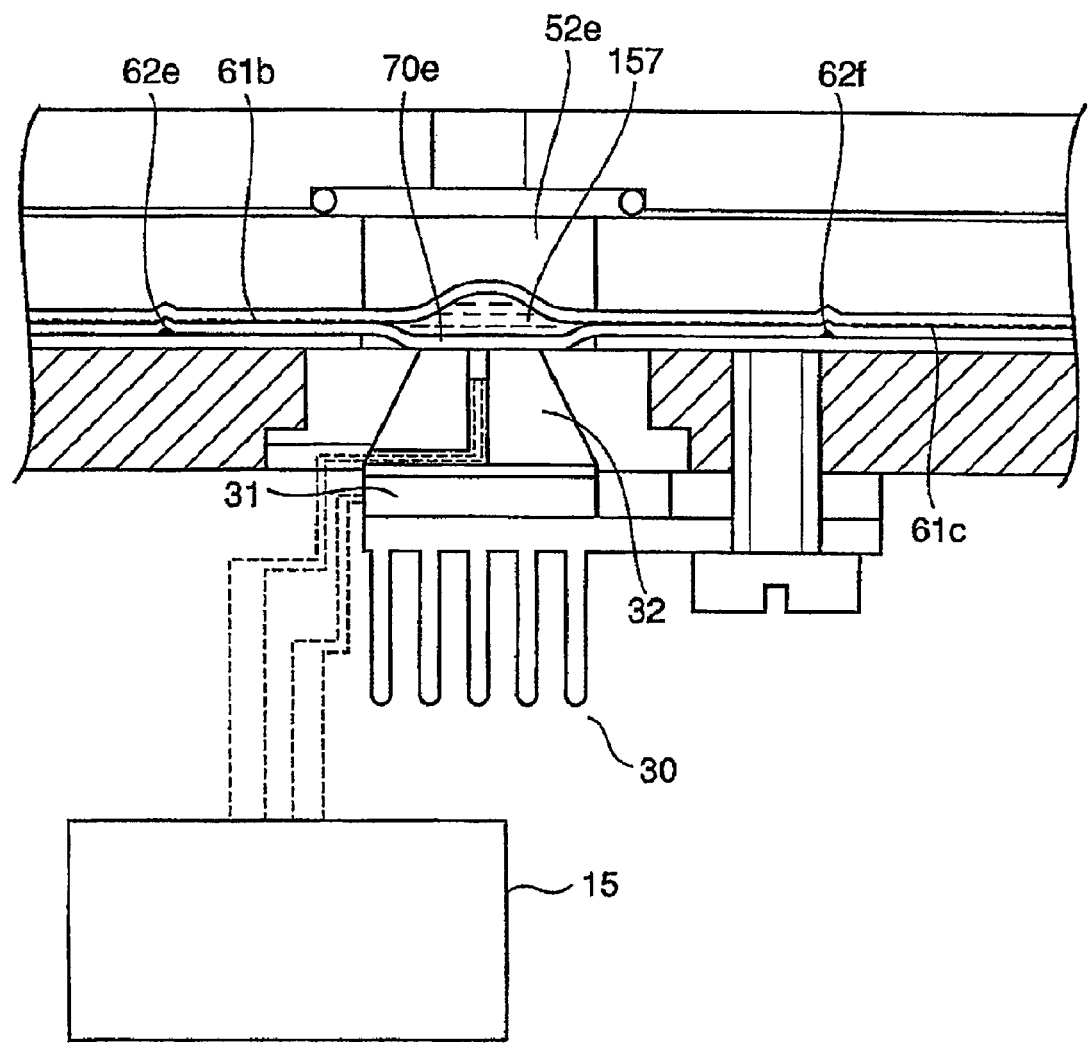
FIG. 6 is a cross-sectional view for illustrating, in Embodiment 1, a state in which injection of the sample into the elastic vessel portion 70e is completed, and both of the shutter channels 62e and 62f are closed.

Next, with reference to FIG. 6, there is described an operation in which, based on the preset program of the controller 15, the temperature control unit 30 performs a predetermined temperature control. FIG. 6 is a cross-sectional view illustrating details of the extraction reservoir 52e and the temperature control unit 30. When the pressure medium is pressurized and applied to the shutter channel 62e from the state illustrated in FIG. 5, the shutter channel 62e closes the channel 61b similarly to the above. Further, the channel 61c is already closed by the shutter channel 62f, and hence the elastic vessel portion 70e has no opened channels. Therefore, the elastic vessel portion 70e is in a closed state. After that, based on the instruction from the controller 15, the temperature control unit 30 is driven. Then, through the Peltier element 31 and the heat transfer member 32, the interior of the elastic vessel portion 70e is heated or cooled. In this case, the sample 157 is in the sealed state, and hence leakage due to a pressure increase caused by a temperature increase does not occur, which enables efficient heating or cooling.

Figure 7:
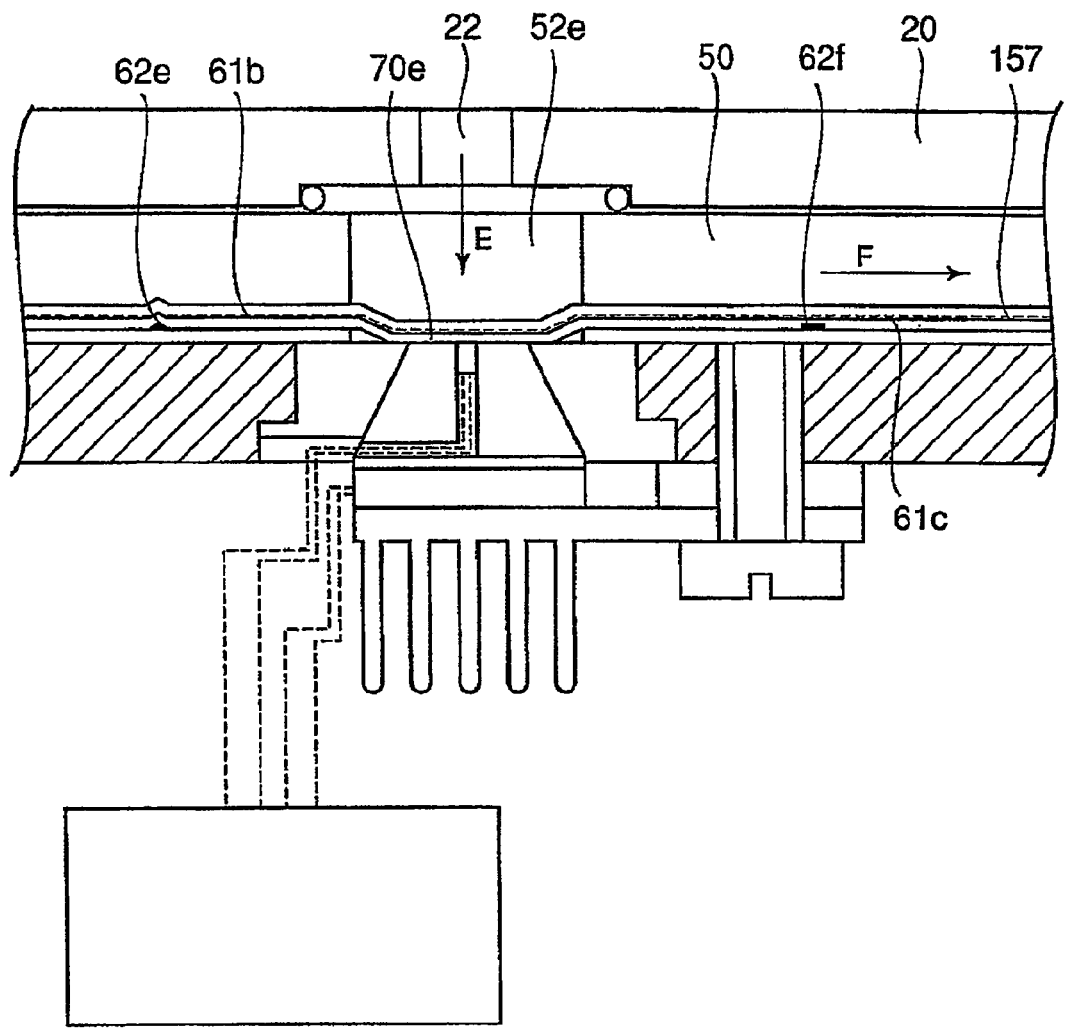
FIG. 7 is a cross-sectional view for illustrating, in Embodiment 1, a step of closing the shutter channel 62e, opening the shutter channel 62f, and applying a pressure to the elastic vessel portion 70e from the direction E so as to discharge the sample to the direction F.

Next, with reference to FIG. 7, an operation of extruding the sample 157 in the elastic vessel portion 70 is described. When the pressure medium pressurized and applied to the shutter channel 62f is released from pressure from the state illustrated in FIG. 6, the shutter channel 62f opens the channel 61c. When the pressure medium is pressurized and applied to an E direction from a pressurizing hole 22 of the cover 20 after that, the sample 157 in the elastic vessel portion 70e is extruded to an F direction through the exclusively-opened channel 61c. As a result, the sample 157 is delivered to the outlet ports 58a, 58b, and 58c through the channel 61c illustrated in FIG. 2 so as to be taken out as an end product. Further, though the structure of the extraction reservoir 52e has been described, the reaction reservoir 52d has the same structure as that of the extraction reservoir 52e.

Figure 8:
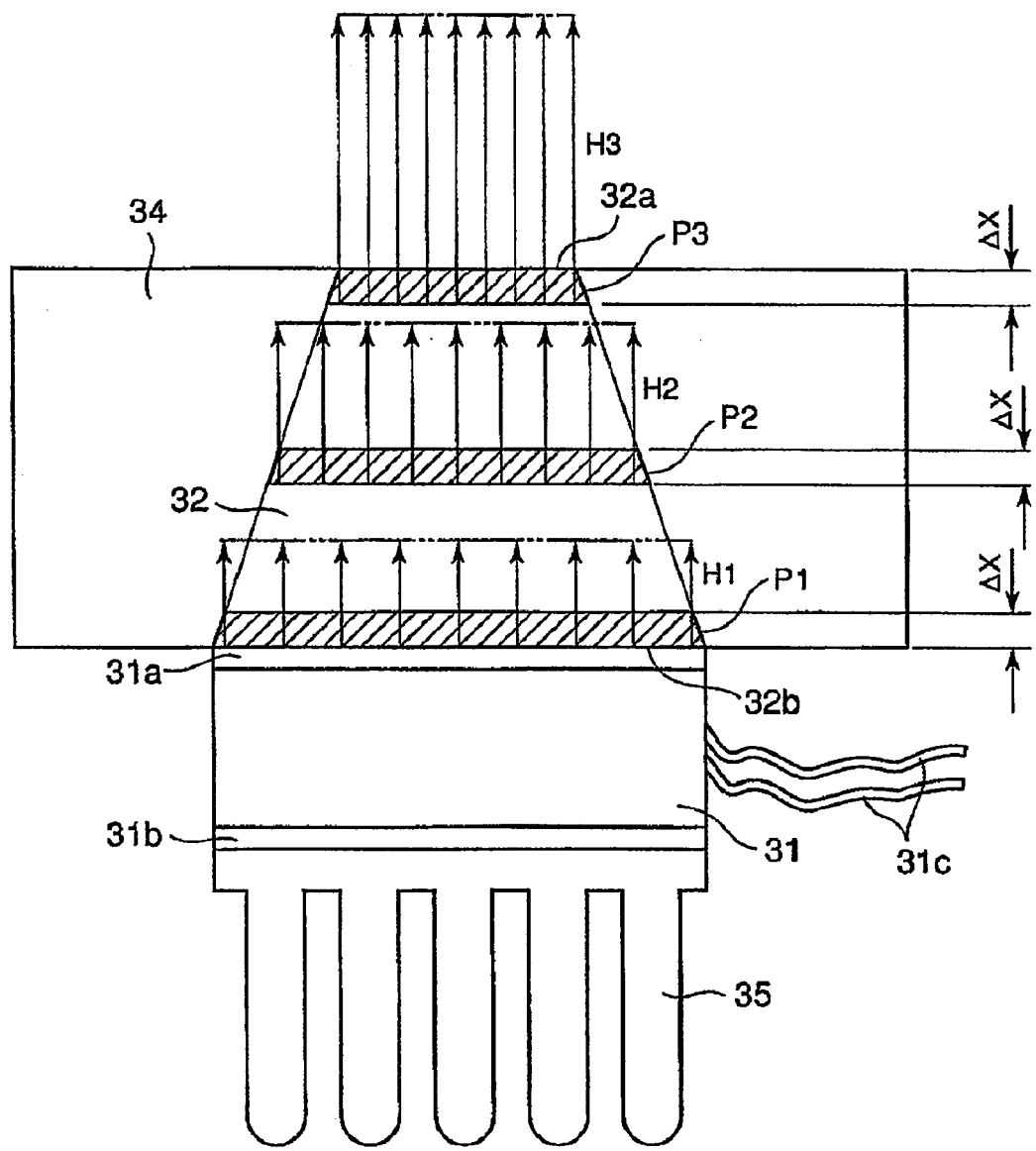
FIG. 8 is a cross-sectional view for illustrating a step of heat transfer occurring in a heat transfer member 32 when the sample is heated.
Figure 9:
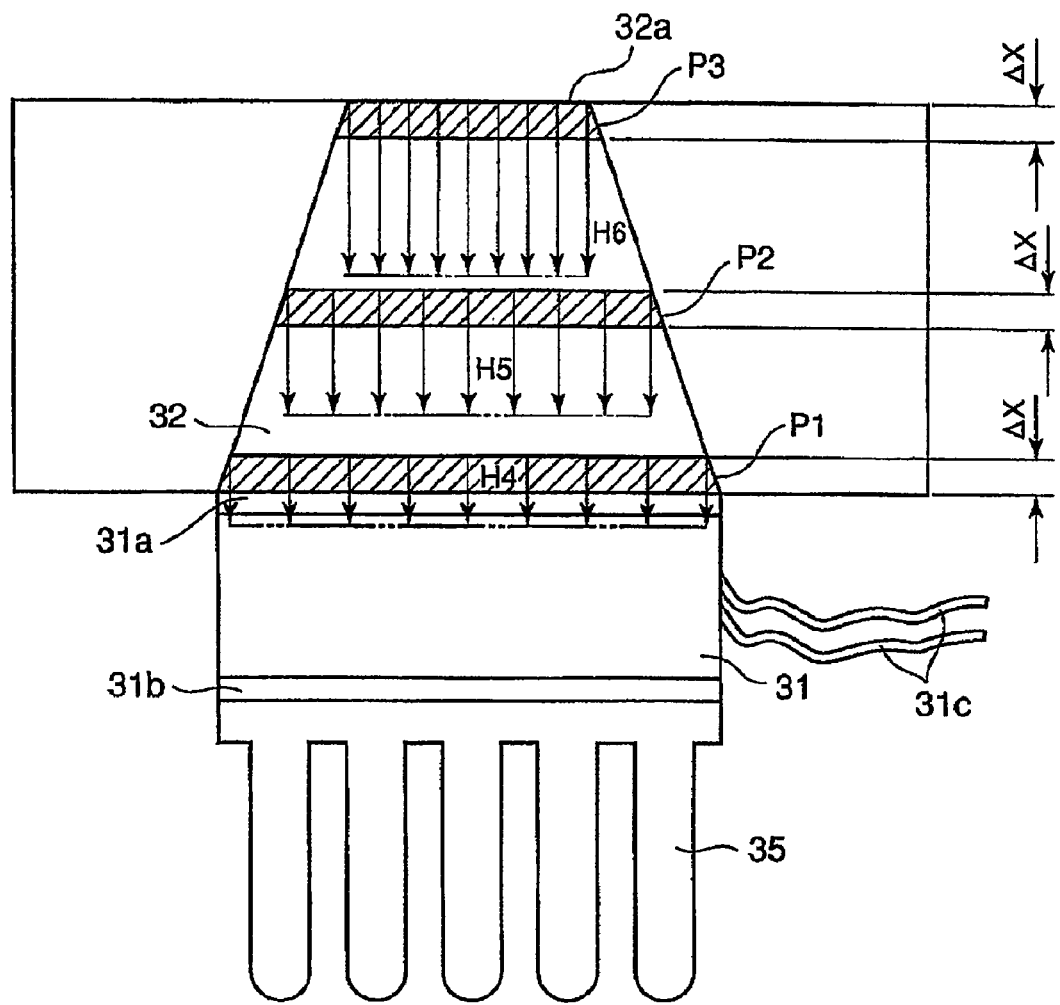
FIG. 9 is a cross-sectional view for illustrating a step of heat transfer occurring in the heat transfer member 32 when the sample is cooled.

Next, an operation of the temperature control unit 30 is described with reference to FIG. 8 and FIG. 9. FIG. 8 is a cross-sectional view illustrating main portions of the temperature control unit 30. As a well known fact, by switching ± poles of voltages applied to the power wires 31c of the Peltier element 31, it is possible to obtain a state in which the heat applying surface 31a generates heat and the heat radiation surface 31b is cooled and a state in which the heat applying surface 31a is cooled and the heat radiation surface 31b generates heat.

First, the state in which the heat applying surface 31a generates heat and the heat radiation surface 31b is cooled is described with reference to FIG. 8. When the heat applying surface 31a of the Peltier element 31 generates heat, the heat shut off from the outside by the heat insulating body 34 transfers heat to a heat transfer body 32, which is an only transferring surface. Distribution of the amount of heat now being transferred from the wide surface 32b of the heat transfer body 32 and supplied to a micro volume P1 based on the wide surface 32b and ΔX is denoted by H1. The amount of supplied heat is further transferred above the heat transfer body 32. Regarding a micro volume P2 in the middle portion of the heat transfer body 32, ΔX is equal to the above and a cross-sectional area is reduced, and hence P1>P2 is established. The volume is reduced and the amount of heat to be supplied is the same, and hence the distribution H2 of the amount of heat in P2 becomes larger than H1. That is, on the upper side of the heat transfer body 32, the distribution of the mount of heat accumulated per unit volume becomes larger. In addition, in the vicinity of the narrow surface 32a to be minimized of the heat transfer body 32, volume based on the area of the narrow surface 32a and ΔX is reduced like P1>P2>P3. As a result, the distribution of the mount of heat becomes H3>H2>H1. That is, regarding the amount of heat supplied to the wide surface 32b of the heat transfer body 32, the distribution of the amount of heat becomes larger while being transferred to the narrow surface 32a. As a result, it is possible to aggregate the amount of heat generated from the Peltier element 31 in a micro portion so as to efficiently heat a PCR amplification reservoir as a micro vessel. Further, the heat radiation surface 31b as a cooling surface of the Peltier element 31 is held in contact with the heat radiation plates 35 with a wide area, and is heated from the atmosphere. As a result, the Peltier element 31 cools the heat radiation surface 31b more, which results in promotion of heat generation of the heat applying surface 31a. That is, as illustrated in FIG. 4, temperature increase speed of the temperature sensor 33 provided in the vicinity of the narrow surface 32a of the heat transfer body 32 and a temperature cycle controlled by the controller 15 becomes faster.

Next, the state in which the heat applying surface 31a is cooled and the heat radiation surface 31b generates heat is described with reference to FIG. 9. When ± poles of voltages to be applied to the power wires 31c are switched, the heat applying surface 31a of the Peltier element 31 is cooled and the heat radiation surface 31b is heated. The object of this step is to radiate the amount of heat transferred from the PCR amplification reservoirs 58a, 58b, and 58c illustrated in FIG. 4 to the narrow surface 32a of the heat transfer member 32. As illustrated in FIG. 7, the distribution of the amount of heat radiated to the micro volume portion P3 based on the narrow surface 32a of the heat transfer member 32 and ΔX is denoted by H6. The outer periphery of the heat transfer member 32 is shut off by the heat insulating member, and the amount of heat is transferred to the lower direction. The micro volume portion P2 based on a micro portion ΔX of the middle portion of the heat transfer member 32 has a cone-like shape and a sectional area thereof is increased, and hence P3<P2 is established. Therefore, distribution of the amount of heat H5 in P2 is H5<H6 in comparison with H6. Therefore, by the amount of increase in volume, the amount of distribution decreases. In addition, the micro volume portion P1 based on ΔX in the vicinity of the wide surface 32b of the heat transfer member 32 increases, and hence P3<P2<P1 is established while the distribution of the amount of heat becomes H4<H5<H6. As a result, speed of heat radiation from the narrow surface 32a becomes faster.

Embodiment 2

Embodiment 2 of this invention is described. Embodiment 2 is partially different from Embodiment 1, and hence points different from Embodiment 1 are described here.

Figure 10:
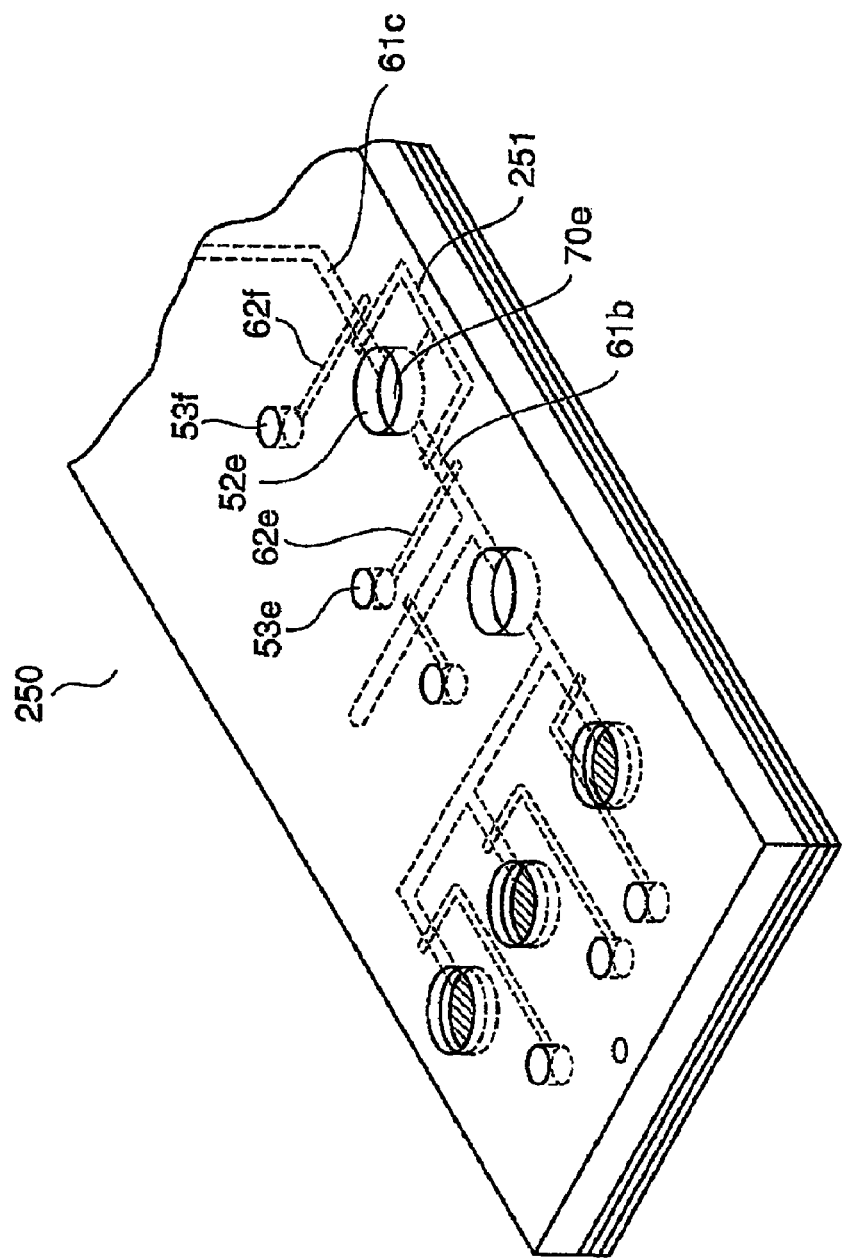
FIG. 10 is a perspective view of part of a microchip 250 of Embodiment 2.

FIG. 10 is a partial perspective view of a microchip 250. The channels 61b and 61c, the shutter ports 53e and 53f, the shutter channels 62e and 62f, the extraction reservoir 52e, and the elastic vessel portion 70e have the same structure as those in Embodiment illustrated in FIG. 2. In addition to the channels 61b and 61c, a closed channel 251 having an E-shape is continuous with the elastic vessel portion 70e. Leading ends of the closed channel 251 are, similarly to the shutter channels 62e and 62f, provided in different layers from the channels 61b and 61c, and are provided below the channels 61b and 61c to constitute intersecting portions with the channels 61b and 61c and terminate. That is, when the elastic vessel portion 70e is packed with the sample, the sample is guided to the closed channel 251, and closes the channels 61b and 61c continuous with the elastic vessel portion 70e.

Figure 11:
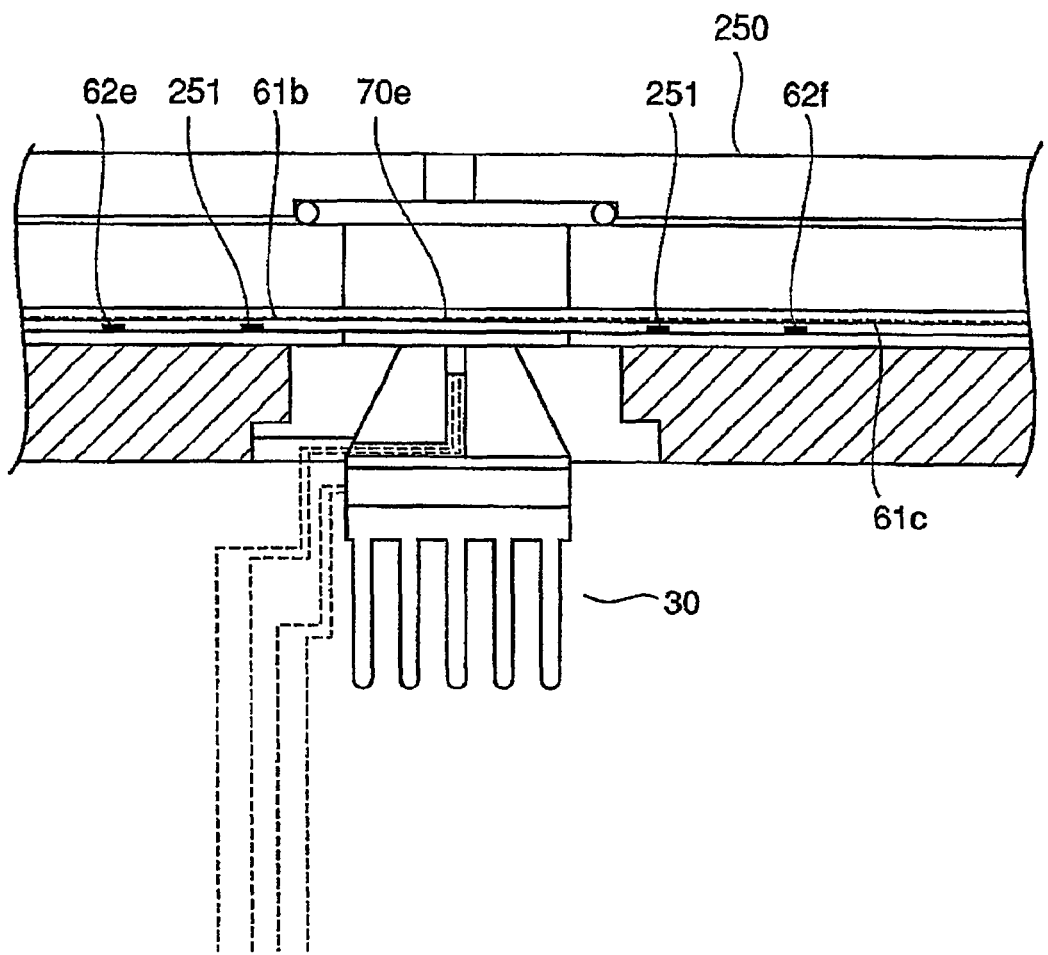
FIG. 11 is a cross-sectional view illustrating the elastic vessel portion 70e, the shutter channels 62e and 62f, and a closed channel 251 of the microchip 250, and their peripheries.

Next, an operation of Embodiment 2 is described with reference to FIG. 11. FIG. 11 is a cross-sectional view illustrating an initial state in Embodiment 2. In the initial state, the pressure medium is not pressurized and applied to the shutter channels 62e and 62f, and hence the channels 61b and 61c are opened. Further, the elastic vessel portion 70e is not packed with the sample, and hence the sample is not guided to the closed channel 251 provided on both sides of the elastic vessel portion 70e, and hence the channels 61b and 61c are opened.

Figure 12:
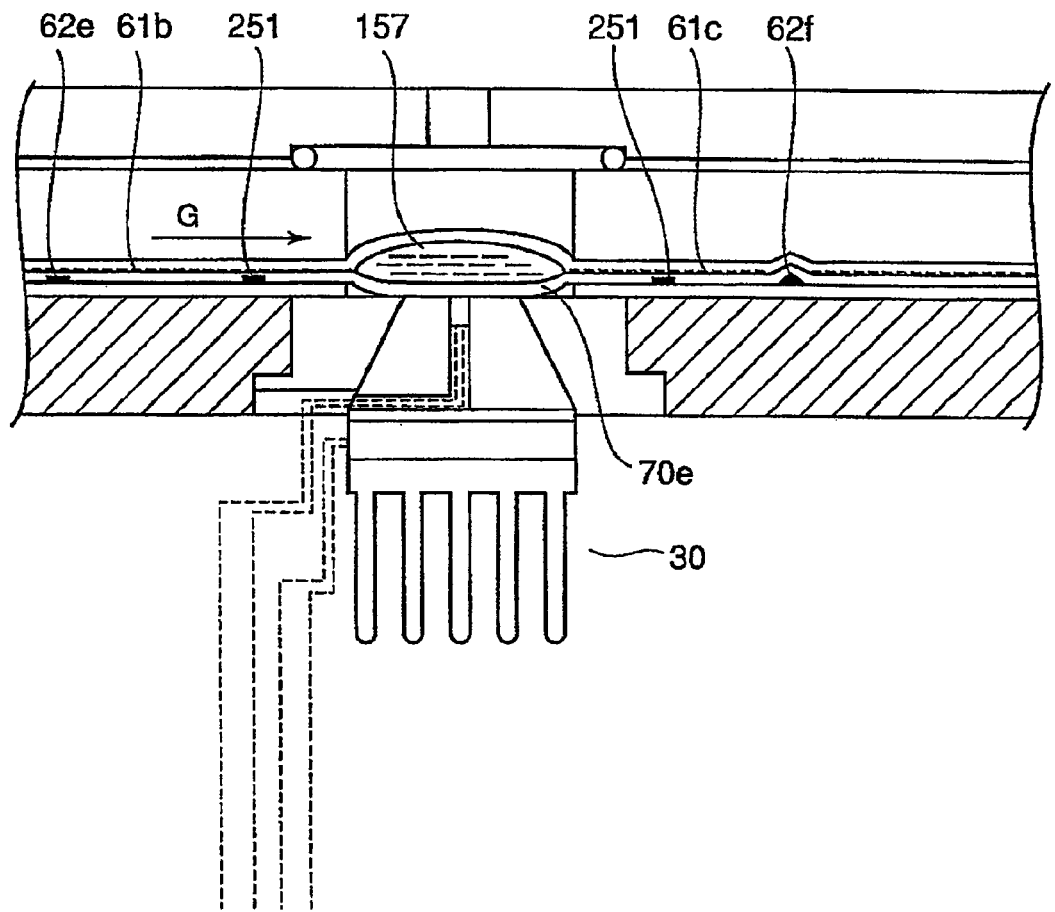
FIG. 12 is a cross-sectional view for illustrating, in the microchip 250, a state in which the shutter channel 62e and the closed channel 251 are opened, the shutter channel 62f is closed, and a sample 157 is injected into the elastic vessel portion 70e.

Next, an operation of a second stage is described with reference to FIG. 12. When the pressure medium is pressurized and applied from the shutter port 53f illustrated in FIG. 10 from the initial state illustrated in FIG. 11, the shutter channel 62f illustrated in FIG. 12 swells, to thereby close the channel 61c. The sample 157 is delivered to the G direction in the channel 61b after that, and is packed in the elastic vessel portion 70e because the shutter channel 62f is closed.

Figure 13:
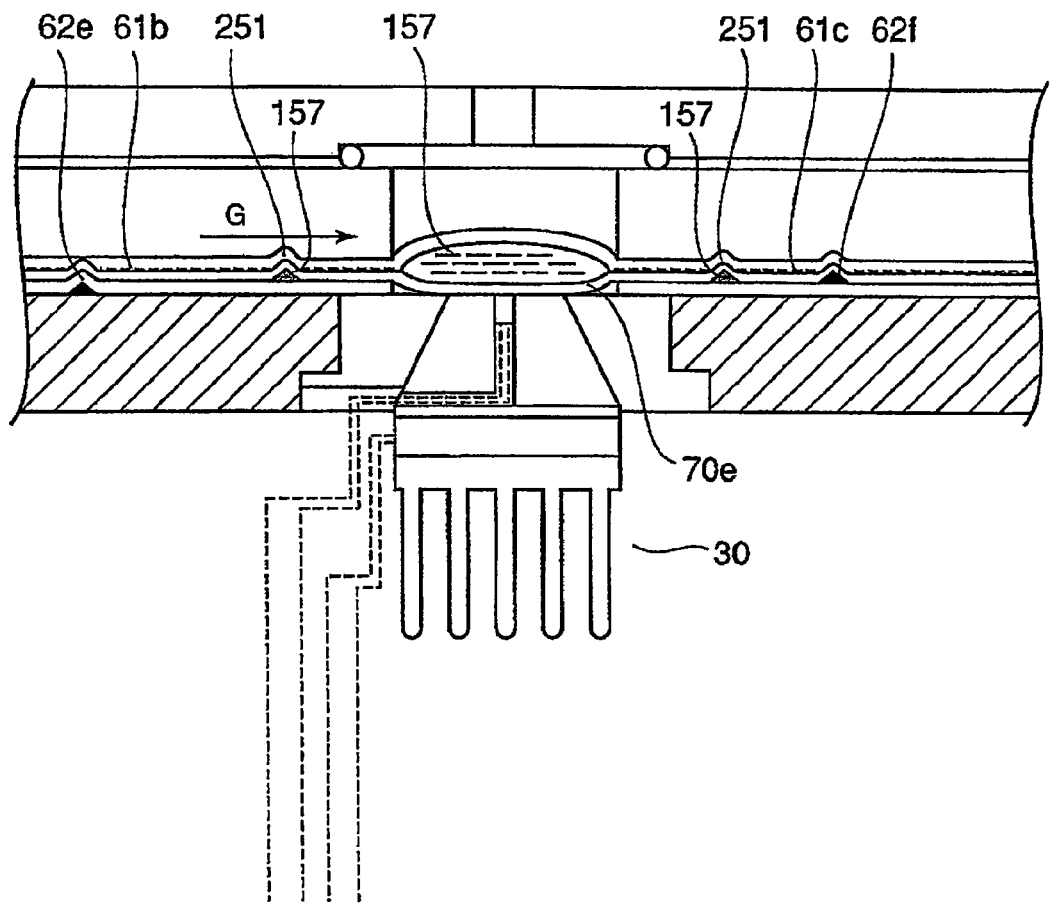
FIG. 13 is a cross-sectional view for illustrating, in the microchip 250, a state in which injection of the sample 157 into the elastic vessel portion 70e is completed, and the shutter channels 62e and 62f and the closed channel 251 are closed.

Next, an operation of a third stage is described with reference to FIG. 13. When the operation of the second stage illustrated in FIG. 12 are continued, the sample 157 is guided to the closed channel 251 via the elastic vessel portion 70e illustrated in FIG. 10. As a result, as illustrated in FIG. 13, the sample 157 guided to the closed channel 251 closes the channels 61b and 61c. After that, when the pressure medium is pressurized and applied to the shutter port 53e illustrated in FIG. 10, the shutter channel 62e illustrated in FIG. 13 expands to close the channel 61b. As a result, the channels 61b and 61c are doubly closed by the shutter channels 62e and 62f and the closed channel 251 so as to have a strong closing force. After that, the temperature control unit 30 is driven, and similarly to the above-mentioned embodiment, the sample 157 in the elastic vessel portion 70e is heated or cooled to a predetermined temperature.

Next, an operation of a fourth stage is described with reference to FIG. 14. After the operation of the third stage illustrated in FIG. 13 is finished, the pressure medium pressurized and applied to the shutter port 53f illustrated in FIG. 10 is released from pressure. As a result, the shutter channel 62f illustrated in FIG. 14 opens the channel 61c. After that, when the pressure medium is pressurized and applied from the pressurizing hole 22 of the cover 20, the sample 157 in the elastic vessel portion 70e is extruded into the channel 61c, which is exclusively opened, to a K direction. As a result, the sample 157 is delivered to the outlet ports 58a, 58b, and 58c illustrated in FIG. 2. After that, the sample 157 is collected by a pipetter, which is a well-known fact, or the like.

As a result, the sample 157 in the elastic vessel portion 70e is subjected to heating or cooling in a strongly-sealed vessel and in a vessel made of an elastic material, and hence the sample 157 is not affected by leakage or the like caused by expansion and contraction by heat. That is, it is possible to obtain the temperature control mechanism having high efficiency and reliability. In Embodiment 1, the channels are closed with respect to the elastic vessel portion 70e only by the shutter channels 62e and 62f. However, in Embodiment 2, with use of the closed channel 251 in addition to the shutter channels 62e and 62f, each of the inflow path 61b and the outflow path 61c is doubly closed with respect to the elastic vessel portion 70e. With this, compared with Embodiment 1, it is possible to obtain a temperature control mechanism having higher reliability.

Embodiment 3

In Embodiments 1 and 2, the sample heated and cooled in the elastic vessel portion 70e is delivered to the outlet ports 58a, 58b, and 58c, and the sample collected through the outlet ports is observed and subjected to analysis. In contrast, in Embodiment 3, after the sample is heated and cooled in the elastic vessel portion 80e, the sample is subjected to observation in the elastic vessel portion 80e without being moved.

Embodiment 3 is described while focusing on differences with Embodiment 2. As illustrated in FIG. 15, a microchip 350 in this embodiment is not provided with the outflow path 61c through which the sample is discharged from the elastic vessel portion 80e. Further, a branch corresponding to the outflow path 61c is not provided to a closed channel 252 corresponding to the closed channel 251 of Embodiment 2.

Further, a difference also lies in that the elastic vessel portion 80e has elasticity and is made of a material having a transmission characteristic to light or a permeability to an electromagnetic wave of at least a certain frequency. With this, it is possible to observe the sample optically or with use of the electromagnetic wave while the sample is contained in the elastic vessel portion 80e. Specifically, for example, by forming the second plate 51b, the third plate 51c, and the fourth plate 51d of polydimethylsiloxane (PDMS) or a polystyrene, the elastic vessel portion 80e is provided with a half-transmission characteristic or a transmission characteristic.

During the operation of the third stage in Embodiment 2, the sample in the elastic vessel portion 80e is observed through the pressurizing hole 22 and the like so as to support analysis of the sample. As one example, when a DNA is used as the sample, the operation of the third stage can be applied to a method called Real Time PCR. In the Real Time PCR method, by optically observing the progress status of a PCR temperature cycle, an increase tendency of an amplified DNA product is measured, and the amount of DNA originally contained in the sample is estimated.

By installing poles and the like in the elastic vessel portion 80e, it is possible to electrochemically observe the sample. With this, it is possible to measure the increase tendency of the DNA product.

Further, by optically observing the status of the sample simultaneously with gradually increasing the temperature in the elastic vessel portion 80e, it is possible to measure the temperature at which double strands of a DNA cleaves.

Embodiment 4

In the above-mentioned embodiments, the diameter of the extraction reservoir 52e is larger than the narrow surface 32a of the heat transfer member 32, and the entire surface of the narrow surface 32a comes into contact with the bottom surface of the elastic vessel portion 70e or 80e. In contrast, in this embodiment, as illustrated in FIG. 16, the diameter of the extraction reservoir 52f is smaller than the narrow surface 32a.

Here, for example, with reference to FIG. 3 and FIG. 16, there is examined a state in which a magnitude relation of the extraction reservoir 52e and the narrow surface 32a in Embodiment 1 is merely reversed. With a small diameter of the extraction reservoir 52e, the elastic vessel portion 70e is further reduced in diameter. When the elastic vessel portion 70e becomes smaller than the diameter of the narrow surface 32a of the heat transfer member 32, the cover 20 presses, through the O-ring 26, a part of the fourth plate 51d below the channel 61b against the narrow surface 32a. As a result, the channel 61b is brought into pressure-contact, and hence, even when the sample 157 is guided to the channel 61b, the part of the fourth plate 51d formed of an elastic member cannot be deflected to a lower direction and is pressure-closed. Therefore, the sample 157 cannot flow into the elastic vessel portion 70e.

In this regard, in this embodiment, as illustrated in FIG. 16, in the narrow surface 32a circled by a circle L of the heat transfer member 32, a cutout portion is provided as indicated by an arrow M, to thereby provide a space in which the part of the fourth plate 51d made of an elastic body constituting a joint portion of the channel 61b and the elastic vessel portion 90e is deflected. With this, resistance when the sample 157 flows into the elastic vessel portion 90e through the channels 61b is decreased, which results in easy injection of the sample.

According to this embodiment, even when the volume of the elastic vessel portion is reduced for heating or cooling the extremely micro sample, it is possible to easily inject the sample of the desired amount into the elastic vessel portion.

Further, in this embodiment, the inflow path and the outflow path into the elastic vessel portion are closed by pressure generated by the sample. When the small amount of sample is heated, the temperature of the sample becomes high and the sample generates high pressure. However, according to this embodiment, the pressure generated by the sample is diverted to the force for closing the channel, and hence it is possible to further efficiently prevent the leakage of the sample from the elastic vessel portion caused by the temperature increase of the sample. As a result, according to this embodiment, it is possible to perform heating with respect to the small amount of the sample, which is liable to generate high pressure.

Embodiment 5

Embodiment 5 is obtained by partially modifying Embodiment 2. Differences with the Embodiment 2 are as described below. That is, a microchip 450 includes, in addition to the main plate 51a, the second plate 51b, the third plate 51c, and the fourth plate 51d, a fifth plate 51e in a layer below the fourth plate 51d. Further, from the main plate 51a to the fourth plate 51d, shutter ports 63 and 64 passes. The shutter port 63 is connected to a shutter channel 253 formed in an unbonded portion between the fourth plate 51d and the fifth plate 51e. Further, the shutter port 64 is similarly connected to an extruding channel 254 formed in the unbonded portion between the fourth plate 51d and the fifth plate 51e.

The shutter channel 253 is provided, of the closed channel 251, in front of a portion intersecting with the channel 61c so as to intersect with the closed channel 251. When the pressure is applied from the shutter port 63 through the pressure medium and the shutter channel 253 is closed, inflow of the sample to the portion intersecting with the channel 61c of the closed channel 251 is stopped.

The extruding channel 254 is provided, of the closed channel 251, from an end portion of a branch intersecting with the channels 61c to a front of the shutter channel 253 so as to overlap the closed channel 251. The extruding channel 254 expands when being pressurized from the shutter port 64 through the pressure medium, to thereby push back the sample in the branch of the overlapped closed channel 251 to the elastic vessel portion 70e.

Up to the third stage, operations are the same as those in Embodiment 2. In the third stage, before applying pressure to the elastic vessel portion 70e, of the sample in the closed channel 251, the sample stopping the flow of the channel 61c is pushed back to the elastic vessel portion 70e by the extruding channel 254. Next, by closing the shutter channel 253, the flow of the sample into the branch stopping the channel 61c of the closed channel 251 is stopped. Further, the pressure medium is taken out from the channel 254.

With this, it is possible to further smoothly discharge the sample from the elastic vessel portion 70e.

Hereinabove, though this invention is described according to Embodiments 1 to 5, it is needless to say that a person skilled in the art can add modifications to the embodiments described above within a scope of the technical idea of this invention.

For example, in the embodiments described above, description was made on the assumption of the temperature control unit having a set of the elastic vessel portion, which is an object of temperature control, the heat transfer member, and the Peltier element. However, it is also possible to provide a plurality of elastic vessel portions in one microchip, and to provide a plurality of heat transfer members and Peltier elements in the analysis device. That is, the elastic vessel portion on the microchip is not limited to one elastic vessel portion, and the number of the temperature control unit corresponding to the elastic vessel portion in the analysis device is not limited to one. When a microchip having a plurality of sample vessels is collectively brought into contact with the heat transfer member corresponding to the plurality of sample vessels, the pressure of the sample for expanding the elastic vessel portion is used in this invention. Therefore, when one inflow path is branched and the elastic vessel portions are provided to each of the branched inflow paths, it is possible to uniform the pressure, by which each elastic vessel portion presses the heat transfer member.

Further, in the embodiments described above, as a device for performing heating and cooling, the Peltier element is exemplified. However, the device may be a heater performing only heating or a cooling device performing only cooling, and hence it is not limited to the Peltier element.

Further, in the embodiments described above, the compressed air is used as a pressurized medium. However, the same effects can be obtained also by other medium capable of transmitting pressure, such as, liquid and gel, and hence the medium is not limited to the compressed air.

Further, in Embodiments 1, 2, and 4, the well-known pipetter means is described as a final taking-out means of the sample. However, the sample may be sequentially delivered to a subsequent analysis means provided on the microchip, for example, a mechanism such as an electrophoretic means.

Further, in Embodiment 4, as a shape of the cutout portion for decreasing resistance of the heat transfer member, the tilting shape is illustrated in FIG. 16. However, the same effects can be obtained also in another shape as long as the shape ensures a space into which a part of the fourth plate 51d is received when receiving the pressure from the cover 20, and hence the shape is not limited.

This invention claims a priority based on Japanese Unexamined Patent Application Publication (JP-A) No. 2007-245905 A filed on Sep. 21, 2007, and hence contents disclosed in the above-mentioned patent application are all incorporated in this application.

The invention claimed is:

1. A temperature control system, comprising:
a vessel portion comprising one or more connecting ports configured for connecting a plurality of channels to the vessel portion and being closed other than with the connecting ports, at least one of the channels being an inflow path for injecting a sample into the vessel portion, the vessel portion further comprising at least one elastic member expanding correspondingly to injection of the sample via the inflow path; and a heat transfer member configured for heating or cooling the sample contained in the vessel portion when the heat transfer member is in contact with the vessel portion, wherein:

expansion of the vessel portion with no injection of the sample keeps the elastic member away from the heat transfer member, and expansion of the vessel portion with injection of a predetermined amount of the sample allows the elastic member to have contact with the heat transfer member, thereby conducting heat between the heat transfer member and the vessel portion through the contact.

2. The temperature control system according to claim 1, comprising, as one of the channels, an outflow path for discharging the sample from the vessel portion, wherein, when the vessel portion containing the predetermined amount of the sample therein is applied with a pressure from an outside, the predetermined amount of the sample is discharged through the outflow path from the vessel portion.

3. The temperature control system according to claim 1, wherein at least a part of one of the channels is formed of an elastic member so that a pressure, which is applied to the part formed of the elastic member of the channel, is controlled so as to control the injection and the discharge of the sample into the vessel portion.

4. The temperature control system according to claim 3, comprising a closed channel, which is connected only to the vessel portion, intersects with the part formed of the elastic member of the channel, and has at least an intersecting portion formed of an elastic member, wherein, correspondingly to the injection of the sample into the vessel portion, the intersecting portion of the closed channel expands and presses another channel intersecting with the closed channel.

5. The temperature control system according to claim 1, wherein at least a part of the heat transfer member is covered with an insulating member.

6. The temperature control system according to claim 1, wherein:

a first elastic plate and a second elastic plate which are laminated with each other are provided;

the first and second elastic plates are partly bonded and partly unbonded with each other, such that an unbonded portion between the first and second elastic plates forms the vessel portion and the channel;

a third elastic plate is provided, the third plate being laminated on a side of the heat transfer member from an elastic plate, which comes into contact with the heat transfer member when the vessel portion expands of the first elastic plate and the second elastic plate;

the heat transfer member comprises, on a surface which comes into contact with the vessel portion, a recessed portion; and the third elastic plate is deformed by being pressed by the expanding vessel portion so that at least a part of the deformed third elastic plate is received in the recessed portion.

7. The temperature control system according to claim 1, wherein the vessel portion has a permeability to an electromagnetic wave of at least a certain frequency.

8. The temperature control system according to claim 1, wherein the heat transfer member comprises a truncated cone fitted into an insulating member.

9. The temperature control system according to claim 1, wherein a heat applying surface of a Peltier element is in contact with a surface of the heat transfer member.

10. The temperature control system according to claim 9, wherein a heat radiation surface of the Peltier element is in contact with a heat radiation plate.

11. The temperature control system according to claim 9, further comprising a temperature sensor and a controller such that the Peltier element is configured to be feedback-controlled from the temperature sensor as programmed by the controller.

* * * * *